United States Patent
Zhao et al.

(10) Patent No.: US 8,000,768 B2
(45) Date of Patent: Aug. 16, 2011

(54) METHOD AND SYSTEM FOR DISPLAYING BLOOD FLOW

(75) Inventors: Meide Zhao, Lisle, IL (US); Ning Meng, Downers Grove, IL (US); Anthony Curcio, River Forest, IL (US)

(73) Assignee: Vassol Inc., River Forest, IL (US)

( * ) Notice: Subject to any disclaimer, the term of this patent is extended or adjusted under 35 U.S.C. 154(b) by 1605 days.

(21) Appl. No.: 11/032,306

(22) Filed: Jan. 10, 2005

(65) Prior Publication Data

US 2006/0155187 A1    Jul. 13, 2006

(51) Int. Cl.
    *A61B 5/05*    (2006.01)
(52) U.S. Cl. ........................................ 600/410; 600/419
(58) Field of Classification Search .......... 600/407–420; 324/307–309
See application file for complete search history.

(56) References Cited

U.S. PATENT DOCUMENTS

| | | | |
|---|---|---|---|
| 3,289,978 A | | 12/1966 | Banaszak |
| 4,216,924 A | | 8/1980 | Fradenburgh et al. |
| 5,368,033 A | * | 11/1994 | Moshfeghi ............... 600/419 |
| 5,394,876 A | | 3/1995 | Ma |
| 6,043,655 A | * | 3/2000 | Makita et al. .............. 324/309 |
| 6,150,814 A | * | 11/2000 | Redpath et al. ............ 324/307 |
| 6,192,264 B1 * | | 2/2001 | Foo et al. .................. 600/413 |
| 6,510,335 B1 * | | 1/2003 | Miyazaki ................... 600/419 |
| 6,782,286 B2 * | | 8/2004 | Miyazaki ................... 600/410 |
| 7,542,622 B1 * | | 6/2009 | Angelini et al. ............ 382/275 |
| 2001/0041833 A1 | | 11/2001 | Bjornerud et al. |
| 2002/0032376 A1 * | | 3/2002 | Miyazaki et al. ........... 600/410 |
| 2002/0035329 A1 | | 3/2002 | Kamiyama |
| 2002/0055917 A1 * | | 5/2002 | Muraca ...................... 707/1 |
| 2002/0151795 A1 | | 10/2002 | Palti |
| 2003/0185450 A1 | | 10/2003 | Garakani et al. |
| 2003/0225328 A1 * | | 12/2003 | DeMeester et al. .......... 600/419 |
| 2004/0027124 A1 * | | 2/2004 | Abe et al. ................... 324/306 |
| 2004/0090230 A1 | | 5/2004 | Appel et al. |
| 2006/0235669 A1 * | | 10/2006 | Charbel et al. .............. 703/11 |
| 2007/0126730 A1 * | | 6/2007 | Goto et al. ................. 345/418 |

FOREIGN PATENT DOCUMENTS

| | | |
|---|---|---|
| EP | 0412824 A2 | 2/1991 |
| EP | 0839497 A1 | 5/1998 |
| EP | 0919832 A2 | 6/1999 |
| EP | 0948929 A2 | 10/1999 |
| EP | 1060706 A1 | 12/2000 |
| GB | 2164155 | 3/1986 |
| WO | WO-0122362 A1 | 3/2001 |

(Continued)

OTHER PUBLICATIONS

Zhao et al, Real-time prescription by three-dimensional vessel localization in cine phase-contrast flow measurement, University of Illinois at Chicago.*

(Continued)

*Primary Examiner* — Sanjay Cattungal
(74) *Attorney, Agent, or Firm* — Schwegman, Lundberg & Woessner, P.A.

(57) ABSTRACT

A method and system are disclosed for presenting anatomical and blood flow information contained in a magnetic resonance imaging (MRI) dataset. A three-dimensional (3D) representation of blood flow is generated which varies with time, referred to herein as a four-dimensional (4D) presentation or display. The system allows the visualization of the dynamics of blood flow and the visualization of anatomical information via the fusion of different types of MRI data sets.

25 Claims, 2 Drawing Sheets

FOREIGN PATENT DOCUMENTS

WO    WO-2006076366 A1    7/2006

OTHER PUBLICATIONS

"International Search Report and Written Opinion for Application No. PCT/US2006/000825, date mailed Jun. 23, 2006", 14 Pages.

Post, F. H., et al., "Fluid Flow Visualisation", *Focus on Scientific Visualisation*, http://web.archive.org/web/20040508100158 http://visualization.tudelft.nl/publications/post1993.pdf, (1993), 1-40.

Westermann, R., et al., "A level-set method for flow visualization.", *Proceedings Visualization 2000*, http://www.ann.jussieu.fr/{frey/papiers/p147-westermann.pdf, (2000), 147-154.

Application Serial No. 06717959.8, Office Action mailed on Jul. 23, 2008, 7 Pages.

"Australian Application No. 2006205025, Examiner's First Report mailed Nov. 11, 2009", 2 pgs.

"European Application No. 06717959.8, Communication Under Rule 71(3) EPC mailed Nov. 13, 2009", 26 pgs.

"European Application Serial No. 06717959.8, Communication mailed Oct. 30, 2007", 6 pgs.

"European Application Serial No. 06717959.8, Response filed Apr. 29, 2008 to Communication mailed Oct. 30, 2007", 4 pgs.

"European Application Serial No. 06717959.8, Response filed Nov. 27, 2008 to Communication mailed Jul. 23, 2008", 19 pgs.

\* cited by examiner

METHOD AND SYSTEM FOR DISPLAYING BLOOD FLOW

BACKGROUND

Many modalities for measuring blood flow in the human body are in use today, including ultrasound and phase contrast magnetic resonance (PCMR), and the results of such measurements are usually displayed in a variety of ways. However, existing medical software for rendering blood flow information typically presents the information in a rather abstract form. A more clinically useful way of displaying blood information would allow the clinician to visualize the dynamics of a plurality of blood flows in an anatomical context. Such a display could be visually analyzed and utilized as a tool for diagnosis and surgery planning in order to treat medical problems such as stroke.

SUMMARY

The present disclosure relates to a method and system for presenting anatomical and blood flow information contained in a magnetic resonance imaging (MRI) dataset. A three-dimensional (3D) representation of blood flow is provided as well as its progression over time, referred to herein as a four-dimensional (4D) presentation or display. Such a system may allow not only the visualization of the dynamics of both arterial and venous flow at the same time, but also the visualization of anatomical information via the fusion of different types of MRI data sets.

DETAILED DESCRIPTION

Figure 1:
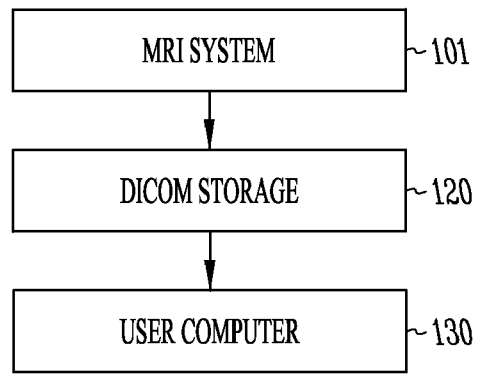
FIG. 1 is a diagram of the components making up an example system.

The present disclosure relates to a system for creating a computer-generated representation of an MRI dataset in all four dimensions of time and space. Particularly, the invention relates to a system and method for transforming an MRI dataset which includes flow-related PCMR images into a temporal sequence of 3D objects, referred to herein as 3D flow images. Such PCMR images may be gated in accordance with detected cardiac activity. The temporal sequence of 3D images may then be displayed as an animation to form a 4D presentation which allows a user to view blood flow in a temporal-spatial context and analyze the time-varying features of the MRI dataset. Anatomical information derived from the MRI dataset or other modalities may also be incorporated into the 4D presentation. In certain embodiments, a user is also able to interact with and manipulate the animation.

In one embodiment, to be described in greater detail below, a user first queries and retrieves a medical data set which includes gated phase contrast magnetic resonance (PCMR) images from a medical dataset storage system, where the PCMR images as well as other data may be in a format such as DICOM (Digital Imaging and Communication in Medicine) which is a standard protocol for sending, receiving and storing medical images. One or more 3D flow surfaces derived from the flow profiles reflected by a 2D phase (or velocity) image are generated in order to create a 3D flow image. Next, the pixel intensities of the flow surfaces making up the 3D flow image are modified by superimposing a 2D magnitude image onto the 3D flow image. The above two steps are applied to each pair of 2D PCMR images in a cardiac cycle so that the dynamics of the pulsatile flow can then be revealed through animating all 3D flow images in the sequence or through manually browsing to thus provide a 4D presentation. This approach provides an intuitive way to visualize the time-varying features of the medical dataset and thus facilitate diagnosis and surgery planning. In order to provide anatomical context to the 4D presentation, a 3D flow image may be fused with a 3D surface rendering of the vasculature through which blood imaged by the 3D flow image flows. The 3D surface rendering of the vasculature may be obtained by MRI or another imaging modality. Fusion of the two 3D objects allows for easy identification of multiple vessels, including both arteries and veins, and when a temporal sequence of such fused 3D images is displayed, allows visualization of the flow direction at each time of a cardiac cycle. The arterial and venous flow can thus easily be distinguished from the context of both the 3D surface rendering of the vasculature and the 3D surface rendering of pulsatile flow profiles. The system may also allow a user to limit the visualization of flow and flow direction inside a selected vessel or vessels, leaving other areas in the 3D flow image flat, in order to help a viewer to focus only on a vessel of interest.

1. System Description

FIG. 1 shows the system components of an exemplary environment appropriate for generating 4D presentations of blood flow as described herein. The environment includes an MRI system 101 as a source of the DICOM images generated for a particular patient. Optionally, an additional imaging system may also be provided which uses a different imaging modality such as CT (Computed Tomography) or ultrasound. The imaging systems are connected via a local network to a DICOM storage device 120 such as a PACS (Picture Archiving and Communication System) that is widely used in the clinical and radiological environment. The PACS system provides the functionality of retrieving DICOM images in response to queries received over the network. The environment also includes one or more user computers 130 where all or part of the 4D visualization software resides. The user computer includes an input device (e.g., keyboard) and a device for displaying the 4D presentations of blood flow to a user (e.g., a monitor). The user computers 130 are connected with the PACS 120 via either a LAN (Local Area Network) or via the internet. (Alternatively, the PACS system may be incorporated into the user computer 130.) The 4D visualization software can take several forms, such as a stand-alone application, an added-on feature of existing medical imaging or management software, or an embedded applet within a web browser. The communication and interaction between user computers 130 and the PACS 120 may be based on internet protocols such as HTTP or HTTPS, depending on the requirement of security.

The MRI system 101 is the primary source of DICOM image data from which a 4D presentation of blood flow may be derived. In magnetic resonance imaging, the spins of specific nuclei (usually hydrogen nuclei) in a tissue are excited by radiofrequency (RF) pulses in the presence of an applied static magnetic field in a selected direction, the magnitude of which is made to spatially vary in a defined time sequence. The precessional frequencies of the excited spins vary in relation to the magnitude of the applied magnetic field and thereby produce a free induction decay (FID) signal from which the spatial locations of the spins can be derived. By applying an excitation RF pulse and a specific sequence of linear spatial variations in the applied magnetic field, referred to as gradient pulses, the resulting FID signal can be interpreted as a carrier waveform amplitude modulated by the Fourier transform of the spatial distribution of spin density in a selected portion of the tissue. The carrier waveform in this case is a complex sinusoid at the spin resonance frequency with no gradient applied (i.e., the Larmor frequency of the spin species). Transformation from the spatial frequency domain, referred to as k-space, to the image position domain can be accomplished by inverse Fourier transforming the k-space signal which is generated after demodulation of the FID signal. The k-space signal is thereby transformed to a spin density function in position space which can be used to generate an image where the intensity of an image pixel varies in accordance with the magnitude of the spin density function at the pixel location. In order to image a selected volume of interest (VOI) in the body, an MRI data set is acquired which is made up of a plurality of slices derived from a two-dimensional (2D) spin density function or a plurality of slabs derived from a three-dimensional (3D) spin density function. As the term is used herein, "image" should be taken to mean either an actual visual representation or the data from which such a representation could be rendered. Similarly, a "pixel" or "voxel" should be taken to mean either a discrete element of an actual 2D or 3D visual representation, respectively, or the corresponding element of a 2D or 3D object from which such a representation could be rendered.

The time sequence of RF excitation and gradient pulses may be manipulated so that the spin density function derived from the k-space signal is dependent upon other parameters in addition to spin density, such as the spin-lattice relaxation time constant $T_1$ or the spin-spin relaxation time constant $T_2$. The time constant $T_1$ relates to the time required for spins to recover longitudinal magnetization after an excitation pulse, the longitudinal magnetization being necessary for the generation of an FID signal following an excitation pulse. A pulse sequence may be designed so that spins with a shorter $T_1$ are weighted more heavily in the spin density function, and a so-called $T_1$ weighted image may be derived from such a spin density function. The time-of-flight (TOF) method of imaging blood flow in tissue involves the use of repeated excitation pulses timed so that blood flowing from an unexcited region into the region excited by the pulses has a greater longitudinal magnetization than the stationary tissue in the excited region. The moving blood thus mimics a tissue with a short $T_1$ and produces an enhanced spin signal. TOF imaging may be used to selectively image blood vessels owing to the moving blood contained within the vessels.

Blood flow may be imaged and quantified by another technique, phase contrast magnetic resonance (PCMR). The k-space signal from the excited spins is a complex signal in which the real and imaginary components modulate the carrier waveform in phase quadrature. Ideally, inverse Fourier transformation of the k-space signal results in a purely real spin density function. Certain artifacts may cause the spin density function to have both real and imaginary parts, but this problem can be circumvented in normal imaging by varying the image pixel or voxel intensity in accordance with the magnitude of the spin density function to create a so-called magnitude image. In PCMR, on the other hand, a bipolar gradient pulse is used to cause flowing spins to acquire a phase which is proportional to the velocity of the spins in the direction of the gradient. After such phase-encoding of velocity, the phase can be extracted from the spin density function to measure the magnitude of blood flow. The extracted phase can also be used to construct an image where the pixel or voxel intensity varies with the phase of the spin density function at the location of the pixel or voxel, called a phase image. A phase image derived from a k-space signal derived after application of an appropriate through-plane bipolar gradient pulse can thus provide a visual representation of the magnitude of blood flow through the plane of the image.

2. Method Description

Figure 2:
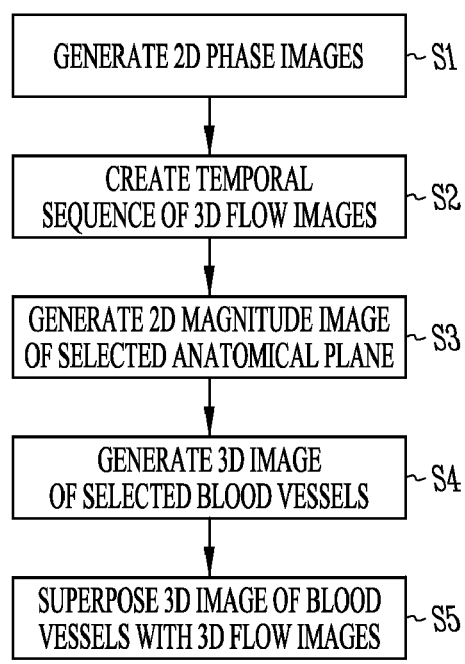
FIG. 2 illustrates the steps involved in an example method for generating 4D flow presentations.

FIG. 2 provides a flowchart of an exemplary method which may be implemented by the system shown in FIG. 1. The 4D visualization software for implementing the method may be stored in a computer-readable medium (e.g., hard disk or optical storage medium) and executed by the user computer. The 4D visualization software in this embodiment may provide a user interface which allows users to query the list of studies and a list of images for each study by providing the patient name or patient ID. After the images of interest are selected and a loading action is invoked, the DICOM image data corresponding to the selected images are retrieved from the PACS into the user computer and processed to generate the 4D flow presentation.

A portion of the DICOM image data received by the user computer is a temporal sequence of 2D phase images representing blood flow through a selected anatomical plane. These 2D phase images are generated at step S1 by the MRI imaging system using PCMR imaging. A particular anatomical plane is selected, and a through-plane gradient is a applied to phase-encode the blood velocity through the plane in the resulting k-space signal. A temporal sequence of such 2D phase images is created, which may be gated so as to be synchronized to the cardiac cycle. In one embodiment, each successive pair of 2D phase images in the temporal sequence represents a systolic phase and a diastolic phase of the cardiac cycle. In another embodiment, each 2D phase image of the temporal sequence represents the same phase of the cardiac cycle.

From the 2D phase images which contain flow or velocity information, the software creates a temporal sequence of 3D flow images at step S2. A 3D flow image is derived from a 2D phase image and includes one or more flow surfaces plotted above or below the anatomical plane at a height corresponding to the phase in the 2D phase image. The height of the flow surface in the 3D flow image may correspond to the phase of the underlying or overlying pixel in the 2D flow image, or may correspond to the phase of a group of underlying or overlying pixels in the 2D flow image. In other words, the location and size information of a pixel in a 2D image is mapped into coordinates of surface element in the X-Y plane, and the intensity of the pixel is mapped into the height (or Z coordinate) for the surface element. Alternatively, several pixels can be grouped together to serve as a larger pixel for the sake of surface generation. For example, 4 (2×2) adjacent pixels can be merged into one pixel with double size in both the X and Y dimensions, and the intensity of the merged pixel can be the average value of the four pixels. In this way, the total number of surface elements used to form a 3D surface (polygons) is decreased, and the amount of resources (memory and CPU) necessary for displaying the 3D surface is reduced. A 3D flow image may be created for each 2D phase image to generate the temporal sequence of 3D flow images. Alternatively, a 3D flow image is created for a 2D phase image and then updated with information from subsequent 2D phase images to generate the temporal sequence of 3D flow images. 2D phase images usually have some artifacts caused by a variety of factors during the image acquisition process. The introduced noise can hinder the understanding of the information contained in the image. A smoothing or blurring algorithm (e.g., a kernel-based convolution smoothing algorithm or an edge-preserving smoothing algorithm) can be used to reduce the effects of those artifacts and at the same time provide a more aesthetic presentation of the real information.

The sequence of 3D flow images may then be serially displayed as an animation to form a 4D flow presentation. During an animation, the temporal sequence of 3D flow images may be displayed at uniformly or arbitrarily spaced time intervals or at time intervals corresponding to the real-time intervals at which the corresponding phase images were acquired. In one embodiment, the sequence of 3D flow images is recorded into a video format for storage in a persistent medium and for subsequent display. In another embodiment, the temporal sequence of 3D flow images is transmitted over a network in the form of pages viewable by browser software. In that case, the 4D presentation may be an interactive one where the user is able to modify features of the 3D flow images. For example, the user may able to selectively flatten one or more of the flow surfaces in the 3D flow image so as to display only those blood flows which are of particular interest.

Once the 3D surfaces of the 3D flow image are created, they can be enhanced in order to render more information. In one embodiment, the color property of every surface element of a 3D surface is changed according to the intensity value of a pixel in another 2D image of interest, such as an image which carries information regarding anatomic structure. For example, the 3D flow images may be enhanced by making the pixel intensities used to form the flow surfaces in the 3D flow image be related to the corresponding pixel intensities in a 2D magnitude image of the same anatomical plane as that of the 2D phase image. Accordingly, a 2D magnitude image of the selected anatomical plane is generated at step S3 using MRI or another imaging modality such as CT. In this way, the different pixel intensities which distinguish arterial blood from venous blood in the 2D magnitude image may also provide that information in the 3D flow image. In the actual 3D flow image, the pixel intensities may be color mapped to a range of colors or gray scale mapped to shades of black and white. Thus, in one example, the color change is implemented through mapping an intensity value of a pixel of the interested 2D image to a triple of R, G, B values. There are many variations in such a color mapping scheme. In one embodiment, a color-map of smooth transition from green to red is used to emphasize the vascular structure. Gray-scale mapping, a special color-map with colors range from black to white, can be used as well, providing a familiar film-like rendering of anatomy structure to the radiologists. Other possibilities of color mapping exist which might be adapted to highlight the different tissues or organs of clinical importance.

There may be multiple vessels including both arteries and veins in the PCMR images, and it may be difficult to identify those vessels from only the rendering of the 3D flow surfaces. In a further enhancement, therefore, anatomical information may be added to the 3D flow images by fusing the 3D flow images with a 3D image of the vasculature. A 3D image of the vasculature can be obtained using a 3D reconstruction algorithm based on time-of-flight (TOF) magnetic resonance images. The two 3D surface objects can also be rendered using transparency, thus allowing viewers to see through a 3D vessel to observe the pulsatile flow and its animation. The flow direction at each time of a cardiac cycle can then be visualized in the 3D fusion image. The arterial and venous flow can easily be distinguished from the context of both the 3D surface rendering of vasculature and the 3D rendering of pulsatile flow surfaces. At step S4 of the exemplary algorithm, a 3D image of selected blood vessels which pass through the selected anatomical plane is generated, where the vessels are rendered as transparent conduits. The 3D image of the selected blood vessels is then superposed or fused with the 3D flow images at step S5 so that the flow surfaces are contained within the transparent vessels.

Figure 3:
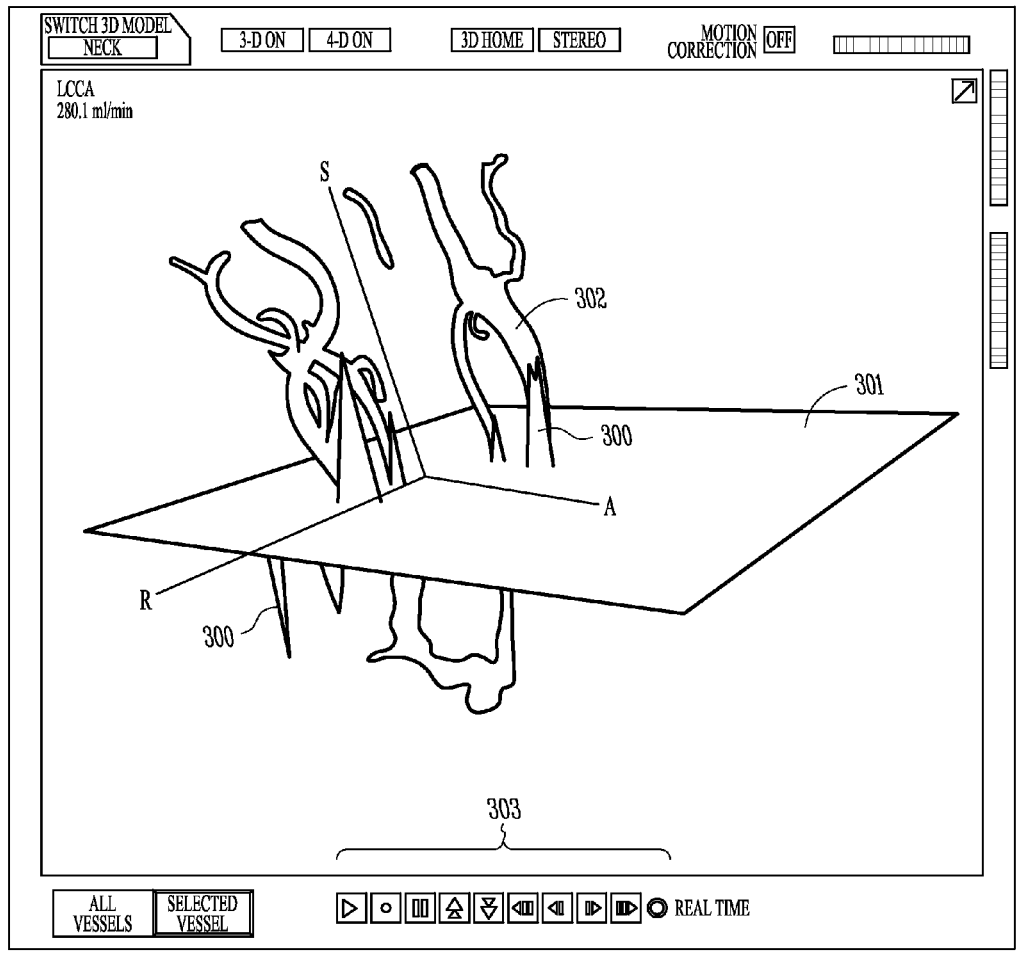
FIG. 3 is a snapshot of a 4D presentation in an example system.

FIG. 3 is the snapshot of an exemplary system in use showing a 4D flow presentation. The bottom panel 303 includes control buttons such as "Start", "Stop", "pause", "forward", "backward", "Fast forward", "Fast backward", and "Real-time animation" etc. The center panel shows an animation of a number of 3D flow surfaces 300 in action, where each of the 3D surfaces in the 3D flow image represents the velocity of a blood flow through the plane 301 along with its surrounding vascular structure 302. The visualization of flow and flow direction can also be limited inside a region of interest, leaving other areas flat in order to help viewers to focus on an interested vessel. The user can manually browse (either forward or backward) these 3D flow images by different strides (e.g., one by one or two by two). The user can also animate the sequence of 3D flow images two ways: uniform and real-time. The uniform way of animation renders each 3D flow image in sequence after every predefined interval. The real-time animation first retrieves the time delay information from DICOM images and attaches this time marker to every 3D flow image. When the animation starts, each frame of the animation stays the amount of time specified by the time marker and thus provides an illusion of animation in real time. Since the time delay might not be identical for all 2D images for a cardiac cycle, the real-time rendering of animation can be non-uniform. In addition, the start, stop and pause controls are also available to maneuver the animation. The 4D flow presentation can be preserved in a persistent medium such as hard disk, CD, DVD or flash memory by saving the presentation in one of many common video formats (AVI, MPEG, and QuickTime, et. al.). The parameters such as frames per second, compression/quality rate can also be adjusted and saved.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A method for displaying blood flow, comprising:

generating a temporal sequence of 2D phase images representing blood flow through a selected anatomical plane using PCMR imaging, wherein each 2D phase image is made up of pixels with each pixel having an intensity corresponding to the phase of a spin density function at the location of the pixel;

for each 2D phase image, deriving a 3D flow image by mapping location and size information of one or more pixels in the 2D phase image into coordinates of a surface element in an X-Y plane corresponding to the anatomical plane and mapping the intensity of the one or more pixels into a height or Z coordinate for the surface element so that the 3D flow image includes one or more flow surfaces plotted above or below the anatomical plane at a height corresponding to the phase in the 2D phase image;

creating a temporal sequence of the derived 3D flow images that correspond to the temporal sequence of 2D phase images; and, displaying the sequence of 3D flow images serially to form a four-dimensional flow presentation.

2. The method of claim 1 wherein the height of the flow surface in the 3D flow image corresponds to the phase of the underlying or overlying pixel in the 2D flow image.

3. The method of claim 1 wherein the height of the flow surface in the 3D flow image corresponds to the phase of a group of underlying or overlying pixels in the 2D flow image.

4. The method of claim 1 wherein a 3D flow image is created for each 2D phase image to generate the temporal sequence of 3D flow images.

5. The method of claim 1 wherein a 3D flow image is created for a 2D phase image and then updated with information from subsequent 2D phase images to generate the temporal sequence of 3D flow images.

6. The method of claim 1 further comprising displaying the temporal sequence of 3D flow images at uniformly spaced time intervals.

7. The method of claim 1 further comprising displaying the temporal sequence of 3D flow images at time intervals corresponding to the real-time intervals at which the corresponding phase images were acquired.

8. The method of claim 1 further comprising transmitting the temporal sequence of 3D flow images over a network in the form of pages viewable by browser software.

9. The method of claim 1 further comprising encoding the temporal sequence of 3D flow images into a video format for storage in a persistent medium.

10. The method of claim 1 further comprising selectively flattening one or more flow surfaces in the 3D flow image.

11. The method of claim 1 further comprising:
generating a 3D image of selected blood vessels which pass through the selected anatomical plane where the vessels are rendered as transparent conduits; and,
superposing the 3D image of the selected blood vessels with the 3D flow images so that the flow surfaces are contained within the vessels.

12. The method of claim 11 wherein the 3D image of selected blood vessels is generated using TOF magnetic resonance imaging.

13. The method of claim 1 further comprising:
generating a 2D magnitude image of the selected anatomical plane using MRI; and,
displaying the flow surfaces of the 3D flow images with pixel intensities matching the corresponding pixel intensities of the 2D magnitude image.

14. The method of claim 13 wherein the pixel intensities are color mapped to a range of colors.

15. The method of claim 13 wherein the pixel intensities are gray scale mapped to a shade of black and white.

16. The method of claim 1 wherein the temporal sequence of 2D phase images is synchronized to the cardiac cycle.

17. The method of claim 16 wherein each successive pair of 2D phase images in the temporal sequence represents a systolic phase and a diastolic phase of the cardiac cycle.

18. The method of claim 16 wherein each 2D phase image of the temporal sequence represents the same phase of the cardiac cycle.

19. A system for displaying blood flow, comprising:
an MRI system configured to generate a temporal sequence of 2D phase images representing blood flow through a selected anatomical plane using PCMR imaging, wherein each 2D phase image is made up of pixels with each pixel having an intensity corresponding to the phase of a spin density function at the location of the pixel;
a computer programmed to: 1) for each 2D phase image, derive a 3D flow image by mapping location and size information of one or more pixels in the 2D phase image into coordinates of a surface element in an X-Y plane corresponding to the anatomical plane and mapping the intensity of the one or more pixels into a height or Z coordinate for the surface element so that the 3D flow image includes one or more flow surfaces plotted above or below the anatomical plane at a height corresponding to the phase in the 2D phase image, and 2) create a temporal sequence of the derived 3D flow images that correspond to the temporal sequence of 2D phase images; and,
wherein the computer is further programmed to display the sequence of 3D flow images serially to form a four-dimensional flow presentation.

20. The system of claim 19 wherein the computer is further programmed to transmit the temporal sequence of 3D flow images over a network in the form of pages viewable by browser software.

21. The system of claim 19 wherein:
the MRI system is further configured to generate a 2D magnitude image of the selected anatomical plane using MRI; and,
the computer is further programmed to display the flow surfaces of the 3D flow images with pixel intensities matching the corresponding pixel intensities of the 2D magnitude image.

22. The system of claim 21 wherein the pixel intensities are color mapped to a range of colors.

23. The system of claim 19 wherein the MRI system is further configured to:
generate a 3D image of selected blood vessels which pass through the selected anatomical plane where the vessels are rendered as transparent conduits; and,
superpose the 3D image of the selected blood vessels with the 3D flow images so that the flow surfaces are contained within the vessels.

24. The system of claim 23 wherein the 3D image of selected blood vessels is generated using TOF magnetic resonance imaging.

25. A non-transitory computer-readable storage medium containing instructions for:
creating a temporal sequence of 3D flow images from a temporal sequence of 2D phase images representing blood flow through a selected anatomical plane using PCMR imaging, wherein each 2D phase image is made up of pixels with each pixel having an intensity corresponding to the phase of a spin density function at the location of the pixel, by: 1) for each 2D phase image, deriving a 3D flow image by mapping location and size information of one or more pixels in the 2D phase image into coordinates of a surface element in an X-Y plane corresponding to the anatomical plane and mapping the intensity of the one or more pixels into a height or Z coordinate for the surface element so that the 3D flow image includes one or more flow surfaces plotted above or below the anatomical plane at a height corresponding to the phase in the 2D phase image, and 2) create a temporal sequence of the derived 3D flow images that correspond to the temporal sequence of 2D phase images; and,
displaying the sequence of 3D flow images serially to form a four-dimensional flow presentation.

\* \* \* \* \*